United States Patent [19]

Flury et al.

[11] Patent Number: 5,506,313
[45] Date of Patent: Apr. 9, 1996

[54] PHOSPHORUS-CONTAINING FLAMEPROOFING AGENTS FOR EPOXY RESIN MATERIALS

[75] Inventors: Peter Flury, Himmelried; Carl W. Mayer, Riehen, both of Switzerland; Wolfgang Scharf, Grenzach-Wyhlen, Germany; Ennio Vanoli, Marly, Switzerland

[73] Assignee: Ciba-Geigy Corporation, Tarrytown, N.Y.

[21] Appl. No.: 301,468

[22] Filed: Sep. 7, 1994

[30] Foreign Application Priority Data

Sep. 9, 1993 [CH] Switzerland ............... 2702/93

[51] Int. Cl.$^6$ .............. C07F 9/12; C07F 9/655; C08G 59/06; C08G 59/30
[52] U.S. Cl. .............. 525/523; 525/525; 528/99; 549/219; 558/162
[58] Field of Search .............. 558/162; 549/219; 528/99; 525/523, 525

[56] References Cited

U.S. PATENT DOCUMENTS

| | | | |
|---|---|---|---|
| 3,056,806 | 12/1962 | Phillips et al. | 260/348 |
| 4,134,876 | 1/1979 | Horner et al. | 260/45.7 P |
| 4,621,123 | 11/1986 | Takagishi et al. | 525/507 |
| 5,072,014 | 12/1991 | Flury | 558/86 |
| 5,130,452 | 7/1992 | Flury et al. | 558/211 |
| 5,132,346 | 7/1992 | Flury | 524/117 |
| 5,278,212 | 1/1994 | Nishihara et al. | 524/141 |

FOREIGN PATENT DOCUMENTS

| | | |
|---|---|---|
| 0412936 | 2/1991 | European Pat. Off. . |
| 0420811 | 4/1991 | European Pat. Off. . |
| 0456605 | 11/1991 | European Pat. Off. . |
| 0509506 | 10/1992 | European Pat. Off. . |

Primary Examiner—Frederick Krass
Attorney, Agent, or Firm—Michele A. Kovaleski

[57] ABSTRACT

The invention relates to compounds of the formula (1)

$$\begin{matrix} RO \\ (RO)_m \end{matrix} > T-[Z], \qquad (1)$$

in which m is 0 or 1,

R is a hydrogen atom or a group of formula

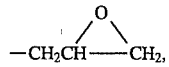

T is either an (m+2)-valent aromatic group or a bisphenylene group,

[Z] is a group of on average 1 to 10 structural units of the formula (3)

$$-Q-T(OR)_{1+m-r}(EB)_r \qquad (3),$$

in which

Q is a group of the formula (4)

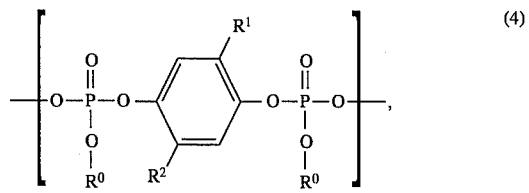

in which $R^0$ is a phenyl radical substituted in a particular manner and $R^1$ and $R^2$ are $C_1$–$C_4$alkyl, and in which, furthermore, EB symbolizes a free valency of the group T, r has one of the values 0, 1 or 1+m
and the structural units of the formula (3) are linked via their free valencies to the group [Z] such that the groups Q in each case alternate with groups T and the group [Z] overall is monovalent. As excellent flameproofing agents which are reactive towards epoxy compounds, the compounds are a useful formulation component for epoxy resin compositions.

9 Claims, No Drawings

PHOSPHORUS-CONTAINING FLAMEPROOFING AGENTS FOR EPOXY RESIN MATERIALS

The present invention relates to novel sterically hindered organophosphate compounds, prelengthened epoxy resins which are obtainable by reaction of these compounds with polyepoxy compounds, and resin compositions based on the phosphorus compounds or the prelengthened epoxy resins.

The use of certain low-halogen, sterically hindered monomeric phosphates as flameproofing agents for polymers, for example for epoxy resins, is already described in EP-A-0 456 605. However, these known compounds contain no functional groups which can react with the epoxy resins, so that they are not incorporated into the resulting polymer network during curing. If such monomeric phosphates are used as flame retardants, however, partial vaporization of the compounds from the plastics material in the course of time cannot always be excluded, so that the flame retardation of the material decreases and/or other properties of the plastics material change adversely.

EP-A-0 420 811 also already describes prelengthened phosphorus-containing epoxy resins which are obtainable by reaction of dialkylpentaerythritol diphosphites with an excess of polyepoxy compounds and, after curing, give a non-combustible or self-extinguishing, halogen-free epoxy material containing chemically bonded phosphorus. However, this material also cannot be completely satisfactory. Thus, for example, the absorption of water by the material is still too high for some applications, such as, in particular, for the production of the laminate base of printed circuits.

The object of the present invention is to provide a flameproofing agent, in particular for epoxy material, which is bonded chemically in the material after curing and thereby meets the demand for a low absorption of water more satisfactorily than conventional materials.

The above objective is met by the instant compounds of the formula (1)

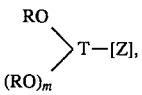  (1)

in which
m is 0 or 1,
R is a hydrogen atom or a group of formula

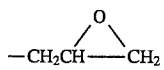

T is either an (m+2)-valent aromatic group having 6 to 14 ring carbon atoms or an (m+2)-valent group which is derived, by removal of (m+2) aromatic hydrogen atoms, from a compound of the formula (2)

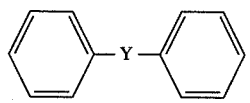  (2)

in which
Y is a chemical structural element chosen from a single bond and the groups of the formula —O—, —S—, >$SO_2$, >C=O and

in which
$R^6$ and
$R^7$ independently of one another in each case are a hydrogen atom or a methyl group, and
[Z] is a group which comprises on average 1 to 10 structural units which are chosen from structural units of the formula (3)

—Q—T(OR)$_{1+m-r}$(EB)$_r$  (3), in which
Q is a group of the formula (4)

  (4)

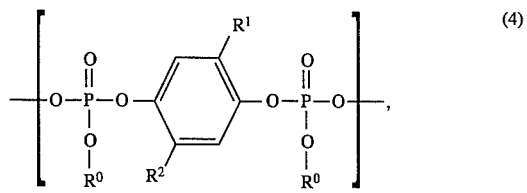

in which
$R^0$ is a radical of the formula (5)

  (5)

$R^1$ and
$R^2$ and
$R^3$ independently of one another in each case are a $C_1$–$C_4$alkyl group,
$R^4$ is a hydrogen atom or a $C_1$–$C_4$alkyl group and
$R^5$ is a hydrogen, bromine or chlorine atom, a hydroxyl group or a group of formula

and in formula (3) furthermore
T has the meaning already given above,
EB symbolizes a free valency of the group T and
r has one of the values 0, 1 or 1+m,
and in which the structural units of the formula (3) are linked via their free valencies to the group [Z] such that the groups Q in each case alternate with groups T and the group [Z] overall is monovalent.

The compounds mentioned are therefore outstandingly suitable both as a flame retardant additional component to curable mixtures based on epoxy resins and for the preparation of prelengthened epoxy resins by reaction with polyepoxy compounds.

If m is 0, [Z] is a group of the formula —[Q—T]$_k$—OR in which k in general is a value from 1 to 10, preferably 2 to 5. On the other hand, if m is 1, the structural units from which the group [Z] is composed are either trivalent (r is 2) or divalent (r is 1) or monovalent (r is 0), corresponding to the formulae —[Q—T]<,

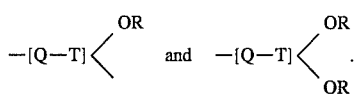 and 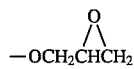

These structural units can be combined in any manner in the group [Z], as long as a group Q always follows a group T (and vice versa) in the resulting chain or chains and the group [Z] overall is monovalent. This is due to the fact that, in cases where m is 1, oligomerization can take place in any manner via one or more terminal hydroxyl groups of the group T.

Preferred compounds of the formula (1) are those in which the group [Z] comprises 2 to about 5 recurring structural units of the formula (3). This can be established, for example, by molecular weight determinations with the aid of gel permeation chromatography.

The radicals $R^1$ and $R^2$ of the compounds according to the invention generally independently of one another can in each case be a methyl, ethyl, n-propyl, i-propyl, n-butyl, i-butyl, sec-butyl or tert-butyl group. Preferably, however, $R^1$ and $R^2$ are in both cases alkyl substituents of the same type, in particular in each case a tert-butyl group.

$R^3$ and $R^4$ likewise independently of one another can be one of the abovementioned alkyl substituents. Methyl is preferred as $R^3$ and $R^4$.

$R^5$ is preferably a hydroxyl group, a group of formula

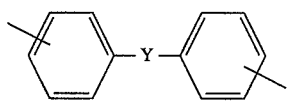

or particularly preferably a hydrogen atom. Halogen radicals $R^5$ are less preferred, since halogen-free compounds of the formula (1) considerably facilitate disposal of plastics materials prepared with these compounds, and it is precisely a great advantage of the compounds according to the invention that with their aid the use of halogen compounds can be dispensed with and a comparable flameproofing action is nevertheless achieved.

Preferred groups T are divalent aromatic rings having 6 to 10 ring carbon atoms or divalent groups of the formula

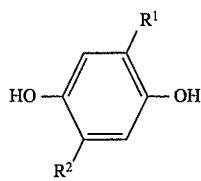

in which Y is as defined above, in particular a methylene or 2,2-propylidene group. Particularly preferred groups T are 1,3-phenylene, 1,4-phenylene, 1,5-naphthylene and 2,2'-bis(4-phenylene)propane, and the group of the formula

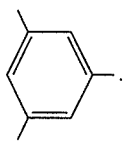

The compounds according to the invention are obtainable, for example, in the following manner:

A diphenol of the formula (6)

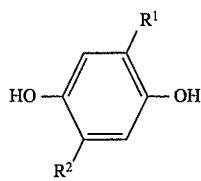

in which
$R^1$ and $R^2$ are as defined above is first reacted with phosphorus trichloride in a suitable solvent under inert conditions, preferably in the approximate molar ratio of 1 to 2 and in the presence of a base, such as pyridine or triethylamine. A phenol of the formula $R^0OH$ in which $R^0$ is likewise as already defined, is added to this reaction mixture, likewise in the approximate stoichiometric ratio of 2 to 1, with respect to the amount of diphenol of the formula (6) employed, and finally, a compound of the formula $T(OH)_{m+2}$, in which T and m are also as already defined above, is added, preferably again in the approximate stoichiometric ratio of 2 to 1, with respect to the amount of diphenol of the formula (6) employed. The phosphite thereby formed is finally oxidized in the customary manner, for example with hydrogen peroxide or peracetic acid, after which the desired phosphate of the formula (1) can be isolated as the end product.

In this preparation process, the number of structural units of the formula (3) from which the group [Z] in the molecule of the reaction product is to be composed can be modified in the desired manner, for example, by varying the stoichiometric ratio of the phenols employed with respect to one another. For example, increasing the content of the phenol of the formula $T(OH)_{m+2}$ with respect to the content of the phenol of the formula (6) leads to an increase in the degree of oligomerization of the compounds according to the invention.

The corresponding glycidylized compounds can be obtained in a manner known per se by reacting the hydroxyl-terminated compounds of formula (1) with epichlorohydrin.

The compounds according to the invention can be added as the reactive constituent to curable mixtures based on epoxy compounds and can be used in this manner for providing the crosslinked epoxy material with a flame resistant finish. The amount of compounds according to the invention employed here can vary within wide limits, and in general 0.1 to 100 parts by weight per 100 parts by weight of epoxy resin, preferably 0.5 to 30 parts, are used. The most favourable amount depends, for example, on the nature of the epoxy resin and on the nature and presence of other components, and can be determined in the individual case by the expert in a simple and quick manner by a few experiments.

Possible epoxy resins here are practically all known compounds which have on average more than one 1,2-epoxide group in the molecule. Such resins can have an aliphatic, aromatic, cycloaliphatic, araliphatic or heterocyclic structure; they contain epoxide groups as side groups, or these groups form part of an alicyclic or heterocyclic ring system. Epoxy resins of these types are generally known and commercially obtainable. Examples of epoxy resins of this type are:

1) Polyglycidyl and poly-(β-methylglycidyl) esters obtainable by reaction of a compound having at least two carboxyl groups in the molecule and epichlorohydrin or glycerol dichlorohydrin or β-methyl-epichlorohydrin. The reaction is advantageously carded out in the presence of bases. Compounds having at least two carboxyl groups in the molecule which can be used are aliphatic polycarboxylic acids. Examples of these polycarboxylic acids are glutaric acid, adipic acid, pimelic acid, subaric acid, azelaic acid, sebacic acid or dimerized or trimerized linoleic acid. However, cycloaliphatic polycarboxylic acids can also be employed, for example tetrahydrophthalic acid, 4-methyltetrahydrophthalic acid, hexahydrophthalic acid or 4-methylhexahydrophthalic acid. Aromatic polycarboxylic acids can furthermore be used, for example phthalic acid, isophthalic acid, trimellitic acid or pyromellitic acid. Carboxyl-terminated adducts, for example of trimellitic acid and polyols, for example glycerol or 2,2-bis-(4-hydroxycyclohexyl)-propane, can likewise also be used.

II) Polyglycidyl or poly-(β-methylglycidyl) ethers obtainable by reaction of a compound having at least two free alcoholic hydroxyl groups and/or phenolic hydroxyl groups and a suitably substituted epichlorohydrin under alkaline conditions or in the presence of an acid catalyst with subsequent treatment with an alkali. Ethers of this type are derived, for example, from acyclic alcohols, such as ethylene glycol, diethylene glycol and higher poly(oxyethylene) glycols, propane-1,2-diol or poly(oxypropylene) glycols, propane-1,3-diol, butane-1,4-diol, poly(oxytetramethylene) glycols, pentane-1,5-diol, hexane-1,6-diol, hexane-2,4,6-triol, glycerol, 1,1,1-trimethylolpropane, bistrimethylolpropane, pentaerythritol, sorbitol and from polyepichlorohydrins. However, they are also derived, for example, from cycloaliphatic alcohols, such as 1,3- or 1,4-dihydroxycyclohexane, bis(4-hydroxycyclohexyl)methane, 2,2-bis(4-hydroxycyclohexyl)propane or 1,1-bis(hydroxymethyl)cyclohex-3-ene, or they have aromatic nuclei, such as N,N-bis(2-hydroxyethyl)aniline or p,p'-bis(2-hydroxyethylamino)diphenylmethane. The epoxy compounds can also be derived from mononuclear phenols, for example from resorcinol or hydroquinone, or they are based on polynuclear phenols, for example on bis(4-hydroxyphenyl)methane (bisphenol F), 2,2-bis(4-hydroxyphenyl)propane (bisphenol A) or condensation products of phenols or cresols with formaldehyde which are obtained under acid conditions, such as phenol novolaks and cresol novolaks. The epoxy compounds of this group II are preferred.

III) Poly-(N-glycidyl) compounds are obtainable, for example, by dehydrochlorination of the reaction products of epichlorohydrin with amines which contain at least two amine hydrogen atoms. These amines are, for example, n-butylamine, aniline, toluidine, m-xylylenediamine, bis(4-aminophenyl)methane or bis(4-methylaminophenyl)methane. However, the poly(N-glycidyl) compounds also include N,N'-diglycidyl derivatives of cycloalkyleneureas, such as ethyleneurea or 1,3-propyleneurea, and N,N'-diglycidyl derivatives of hydantoins, such as of 5,5-dimethylhydantoin.

IV) Examples of poly-(S-glycidyl) compounds are di-S-glycidyl derivatives which are derived from dithiols, for example ethane-1,2-dithiol or bis(4-mercaptomethylphenyl) ether.

V) Examples of epoxy compounds in which the epoxide groups form part of an alicyclic or heterocyclic ring system are, for example, bis(2,3-epoxycyclopentyl) ether, 2,3-epoxycyclopentylglycidyl ether, 1,2-bis(2,3-epoxycyclopentyloxy)ethane, bis(4-hydroxycyclohexyl)methanediglycidyl ether, 2,2-bis(4-hydroxycyclohexyl)propanediglycidyl ether, 3,4-epoxycyclohexylmethyl 3,4-epoxycyclohexanecarboxylate, 3,4-epoxy-6-methyl-cyclohexylmethyl 3,4-epoxy-6-methylcyclohexanecarboxylate, di(3,4-epoxycyclohexylmethyl) hexanedioate, di(3,4-epoxy-6-methylcyclohexylmethyl) hexanedioate, ethylene-bis(3,4-epoxycyclohexanecarboxylate), ethanediol di(3,4-epoxycyclohexylmethyl) ether, vinylcyclohexene dioxide, dicyclopentadiene diepoxide or 2-(3,4-epoxycyclohexyl-5,5-spiro-3,4-epoxy)cyclohexane-1,3-dioxane.

However, epoxy resins in which the 1,2-epoxide groups are bonded to different hetero atoms or functional groups can also be used. These compounds include, for example, the N,N,O-triglycidyl derivative of 4-aminophenol, the glycidyl ether glycidyl ester of salicylic acid, N-glycidyl-N'-(2-glycidyloxypropyl)-5,5-dimethylhydantoin or 2-glycidyloxy-1,3-bis(5,5-dimethyl-1-glycidylhydantoin-3-yl)propane.

Mixtures of epoxy resins can of course also be employed, as can prelengthened epoxy resins, i.e. prereacted adducts, which still contain free epoxide groups, of one or more epoxy resins with one or more compounds which contain, per molecule, at least two functional groups which react with epoxide groups. Compounds which can react with epoxide groups are, for example, aliphatic or aromatic diamines and diols. To prepare the prelengthened epoxy resins, these are reacted with an excess of epoxy resins (excess epoxide groups with respect to the functional groups which are reactive with epoxide groups). If appropriate, the prelengthened epoxy resins thus obtained can also be lengthened further in the same manner.

A particularly preferred embodiment comprises advanced epoxy resins which are obtainable by reaction of a mixture which comprises at least one compound of the formula (1) which has free hydroxyl groups and at least one polyepoxy compound, preferably a glycidyl ether based on bisphenol A or bisphenol F or a novolak, in particular a phenol-formaldehyde or a cresol-formaldehyde novolak. The present invention therefore likewise relates to these advanced epoxy resins. Since the advanced epoxy resins according to the invention in general are solid, they can also be dissolved in a suitable solvent, such as methyl ethyl ketone, if appropriate. This is preferably done while heating.

The invention also relates to compositions which comprise a compound of the formula (1) together with an epoxy resin, and compositions which comprise an advanced epoxy resin based on a compound of the formula (1).

The compositions according to the invention furthermore can comprise other customary additives and modifying agents in an amount suitable for the particular purpose, for example heat stabilizers, light stabilizers, UV absorbers, antioxidants, antistatic agents, preservatives, adhesion promoters, fillers, pigments, lubricants, foaming agents, fungicides, plasticizers, processing auxiliaries, other flame retardant additives and agents for reducing the evolution of smoke.

Additional flame retardants which can be employed together with the compounds of the formula I used according to the invention are, for example, phosphorus-containing salts, for example ammonium polyphosphates and aluminium phosphates, and in addition aluminium hydroxides, such as $Al(OH)_3$, and likewise magnesium hydroxide, quartz, zinc borate or other phosphorus compounds, for example the compounds described in EP-A-0 412 936, or tertiary phosphine oxides, for example the compound of the formula

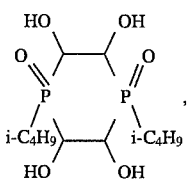

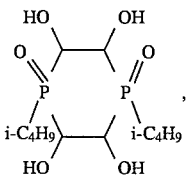

which is also commercially obtianable under the name Cyagard®RF-1204. The compound of the formula

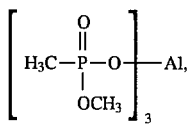

which is commercially obtainable under the name REOFLAM®410, is also particularly suitable as an additional flame retardant for the compositions according to the invention. The compounds according to the invention can of course also be employed together with halogen-containing flame retardants, for example with tetrabromobisphenol A or the diglycidyl ether derived therefrom. In some cases, combinations of the compounds according to the invention, employed either per se or in the form of an advanced epoxy resin, with one or more other flameproofing agents, in particular halogen-free flameproofing agents, for example those mentioned above, result in particularly good properties.

An expressly preferred composition according to the invention thus comprises an advanced epoxy resin based on one of the compounds according to the invention, preferably in an amount of 10 to 40 parts by weight, and another phosphorus-containing flameproofing agent, preferably in an amount of 5 to 40 parts by weight. If appropriate, a water-insoluble, non-hygroscopic filler which is inert towards the resin can also be present as a further flame retardant component, preferably in an amount of 20 to 80 parts by weight. When the compounds according to the invention are used, excellent flame retardation (class V-0 or V-1 in accordance with UL 94) is also achieved without problems with a comparatively low content of such filler components which are not reactive with the resin. Another particularly preferred phosphorus-containing flameproofing agent with the compositions according to the invention is the compound of the formula already mentioned above, in particular together with aluminium trihydrate. Glycidyl ethers based on bisphenol A or bisphenol F or on phenol-formaldehyde and cresol-formaldehyde novolaks are also particularly preferred epoxy resins for advancement in these specific compositions.

The compositions according to the invention can be prepared in a known manner, for example by premixing individual components and subsequently mixing these premixes, or by mixing all the components by means of customary devices, such as stirred tanks or a dispersing unit, if appropriate at slightly elevated temperature.

The compositions according to the invention can be made up as one-component or two-component mixtures, depending on the wishes of the user. In the first case, they comprise, as a further constituent, a customary, preferably latent hardener for epoxy resins, for example dicyandiamide. In the second case, they form the polymer component of the two-component system and are mixed with a component comprising a customary hardener for epoxy resins only shortly before use.

The compositions according to the invention can be employed quite generally for the production of cured products and are suitable for all intended uses where curable mixtures based on epoxy resins are employed in industry, for example as coating materials, varnishes, moulding materials, dipping resins, casting resins, impregnating resins, laminating resins, one- or two-component adhesives or as matrix resins, in particular for enveloping and impregnating objects. A particularly preferred field of use is use as a laminating resin for the production of the laminate base of printed circuits.

Unless stated otherwise in the following examples, the amounts are stated in grams.

EXAMPLE 1

Preparation of the Compound

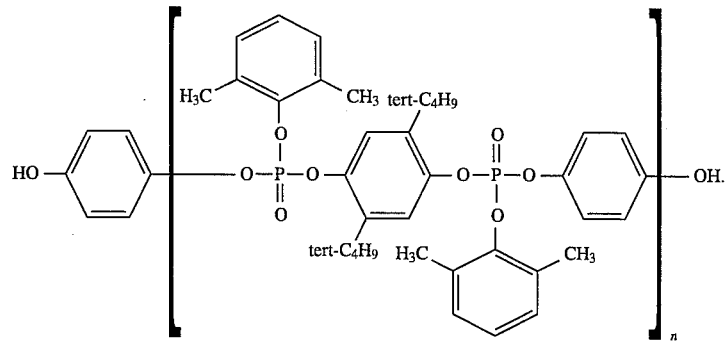

3.78 kg of 2,5-di-tert-butylhydroquinone (17 mol), 3 kg of ethyl acetate and 0.170 kg of pyridine are mixed under dry nitrogen and while stirring thoroughly in a reaction vessel with an intensive condenser and waste gas scrubbing unit, and the mixture is heated to an internal temperature of 60° C. 4.67 kg of phosphorus trichloride (34 mol) are added at 60° C. in the course of 30 minutes. The resulting mixture is refluxed for about 1 hour (internal temperature about 74° C.). A solution of 4.15 kg of 2,6-dimethylphenol (34 mol) in 3 kg of ethyl acetate is then added at an internal temperature in the reaction vessel of 75°–77° C. in the course of 1 hour, and the brown solution formed is stirred under reflux for 1 hour and 30 minutes and then cooled to about 25° C. A solution of 3.74 kg of hydroquinone (34 mol) in 9 kg of ethyl acetate and 2.7 kg of acetone is added at 25° C. in the course of about 2 minutes, 4.66 kg of triethylamine (46 mol) are then added and the mixture is stirred for a further 30 minutes. 3.86 kg of 30% strength $H_2O_2$ are then added in the course of about 1 hour, the temperature in the reaction vessel being kept between 30° and 35° C., and the mixture is stirred for a further 2 hours. It is washed twice with 1N HCl and once with 0.1N HCl, and the organic phase is separated off, dried with sodium sulphate and freed from the solvent in vacuo. The resulting solid product is finally dried further under a high vacuum for another 30 minutes.

8.33 kg of the desired product (71% of theory) are obtained. From the GPC, $M_n$=700 and $M_w$=2947. The analysis of the product is as follows:

|  | C [%] | H [%] | P [%] |
|---|---|---|---|
| found: | 64.35 | 6.28 | 8.22 |
| calculated: | 65.28 | 6.00 | 8.02 |

The chlorine content of the product is less than 0.3%.

EXAMPLE 2

Preparation of the Compound

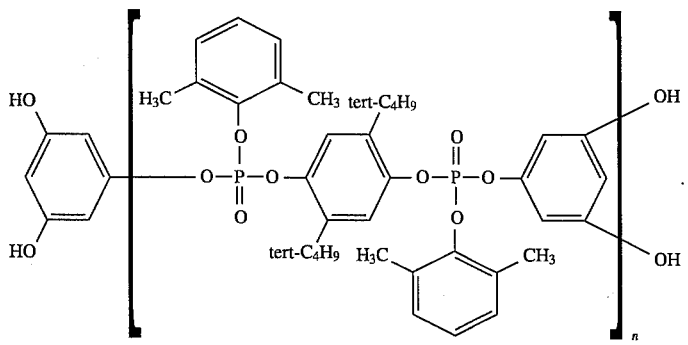

22.22 g of 2,5-di-tert-butylhydroquinone (0.1 mol), 17.5 g of ethyl acetate and 1.05 g of pyridine are mixed under dry argon and while stirring thoroughly in a reaction vessel with an intensive condenser and waste gas scrubbing unit. 27.5 g of phosphorus trichloride (0.2 mol) are added to the mixture. The resulting mixture is heated slowly and kept under reflux for 1 hour. A solution of 24.4 g of 2,6-dimethylphenol (0.2 mol) in 17.5 g of ethyl acetate is then added in the course of about 10 minutes, and the brown solution formed is stirred under reflux for 1 hour and 30 minutes and then cooled to room temperature. A solution of 25.22 g of 1,3,5-trihydroxybenzene (0.2 mol) in 52 g of ethyl acetate and 15.5 g of acetone are added in the course of about 15 minutes, while cooling with ice, 27.35 g of triethylamine (0.27 mol) are then added in the course of 30 minutes, while further cooling with ice, and the mixture is stirred for another 30 minutes. 22.67 g of 30% $H_2O_2$ are then added slowly, while cooling thoroughly, and the mixture is stirred again for 2 hours. Thereafter, the desired product is isolated and dried in accordance with Example 1.

The resulting brown resinous product has a softening point of 156.6°–171.2° C. The analysis of the product is as follows:

|  | C [%] | H [%] | P [%] |
|---|---|---|---|
| found: | 61.20 | 6.53 | 8.13 |
| calculated: | 62.53 | 6.00 | 7.68 |

The hydroxyl content of the product is 5.65 meq of OH/g.

EXAMPLE 3

The advanced epoxy resins 1 to 4 are prepared from the particular components shown in the following table:

| Component | Resin 1 | Resin 2 | Resin 3 | Resin 4 |
|---|---|---|---|---|
| Bisphenol-A-di-glycidyl ether[1] | 100.00 | 100.00 | 100.00 | 100.00 |
| Compound from Example 1 | 20.00 | 20.00 | 20.00 | 20.00 |
| Diaminotriazine | — | 4.00 | — | — |
| Diethyltoluene-diamine | — | — | 4.00 | — |
| Diaminodiphenyl-sulphone | — | — | — | 6.00 |
| o-Cresol novolak[2] | 10.00 | — | — | — |
| Methyl ethyl ketone | 32.50 | 31.00 | 31.00 | 31.50 |

[1]Epoxy value: 5.29–5.41 eq/kg; viscosity (25° C.): 12000–14000 mPa · s
[2]Melting point 100° C.; hydroxy value: 8.5 eq/kg To prepare the advanced resins, the bisphenol A diglycidyl ether is heated to 100°–120° C. Thereafter, the compound from Example 1 is added and the mixture is reacted at 170° C. until the epoxy value remains constant. The other components are then in each case added, and the mixture is again allowed to react until the epoxy value remains constant. The still hot resin is then dissolved in the stated amount of methyl ethyl ketone as the solvent.

Impregnating solutions IL1, IL2, IL3 and IL4, the further composition of which can be seen from the following table, are prepared in each case using resins 1, 2, 3 and 4.

| Component* | IL1 | IL2 | IL3 | IL4 |
|---|---|---|---|---|
| Resin: No. | 1 | 2 | 3 | 4 |
| Amount | 125.00 | 125.00 | 125.00 | 125.00 |
| Dicyandiamide[3] | 36.20 | 35.20 | 40.10 | 37.10 |
| Cyagard ® RF 1204 | 20.00 | 20.00 | 20.00 | 20.00 |
| Apyral ® 4[4] | 40.00 | — | 40.00 | 40.00 |
| 2-Methylimidazole | 0.08 | — | 0.10 | 0.08 |

[3]The weight data are based on a 10% solution of dicyandiamide in methyl glycol
[4]Aluminium oxide trihydrate
*If desired, the customary amount of a flow agent can also be added to the above impregnating solutions without the properties described below thereby changing.

Laminates LAM1, LAM2, LAM3 and LAM4 are produced with the aid of impregnating solutions IL1, IL2, IL3 and IL4. For this, glass fabric is first impregnated with the impregnating solution and the entire system is dried in an oven at 170° C. for a few minutes. The resulting prepreg is cut into appropriate pieces. Eight layers of this prepreg are placed between 2 layers of copper foil and pressed to the finished laminate by pressing at 170° C. for one hour. The resulting laminates have the properties shown in the following table.

| Property | LAM1 | LAM2 | LAM3 | LAM4 |
|---|---|---|---|---|
| Tg 1[5][°C.] | 131.5 | 136.5 | 138.7 | 141.2 |
| Tg 2[5][°C.] | 133.5 | 137.8 | 139.40 | 143.7 |
| Absorption of NMP[6] [%] | 0.24 | —** | 0.08 | 0.08 |
| Absorption of $H_2O$[7] [%] | 0.40 | —** | 0.37 | 0.40 |
| Pct[8] | p | —** | p | p |
| Flame retardation[9] | V-0 | V-0 | V-0 | V-0 |
| Burning time [s] | 14 | 42 | 25 | 34 |
| Phosphorus content [%] | 3.05 | 4.11 | 3.09 | 3.09 |

**not determined
[5]The glass transition temperatures of the laminate specimens were determined with the aid of differential scanning calorimetry. Tg 1 indicates the value for the glass transition temperature resulting from the first measurement, while Tg 2 indicates the value obtained when the specimen is subjected to a corresponding measurement again after the first measurement.
[6]Absorption of N-methylpyrrolidone by a 5 × 5 cm laminate specimen at 23° C. after 30 minutes. The thickness of the specimen corresponds to the thickness of the resulting laminate of about 1.6 mm.

EXAMPLE 4

100 g of a polyglycidyl ether based on a phenol-formaldehyde novolak (epoxy value 5.5–5.7 eq/kg) and 132 g of the compound from Example 1 are dissolved in 100 g of methyl ethyl ketone, while heating. 38.50 g of a 10% solution of dicyandiamide and 40 g of aluminium oxide trihydrate are then added and the mixture is homogenized by means of a dispersing unit. Addition of 0.02 g of 2-methylimidazole as an accelerator and further stirring follow. A laminate (LAM5) which has the following properties is prepared analogously to Example 3 with the aid of this impregnating solution.

| Property | LAM5 | Property | LAM5 |
|---|---|---|---|
| Tg 1[5] [°C.] | 131.0 | Pct[8] | P |
| Tg 2[5] [°C.] | 129.6 | Flame | |
| Absorption of NMP[6] [%] | 0.15 | retardation[9] | V-1 |
| Absorption of $H_2O$[7] [%] | 0.33 | Burning time [s] | 88 |

[5,6,7,8,9]See under Example 3

EXAMPLE 5

The advanced epoxy resins 6 to 9 are prepared from the particular components stated in the following table.

| Component | Resin 6 | Resin 7 | Resin 8 | Resin 9 |
|---|---|---|---|---|
| Bisphenol A diglycidyl ether[1] | 66.15 | 61.55 | 61.24 | 53.25 |
| Diaminodiphenylsulphone | 5.73 | 5.00 | 5.00 | 5.72 |
| Polyglycidyl ether from Example 4 | — | — | — | 12.90 |
| Tetraglycidyl ether[11] | — | 12.48 | 12.48 | — |
| TBBA[10] diglycidyl ether | 11.03 | — | 6.31 | 11.03 |
| TBBA[10] | — | 5.99 | — | — |
| Compound from Example 1 | 17.10 | 14.98 | 14.97 | 17.10 |

[1]See under Example 3
[10]TBBA = Tetrabromobisphenol A
[11]Formula:

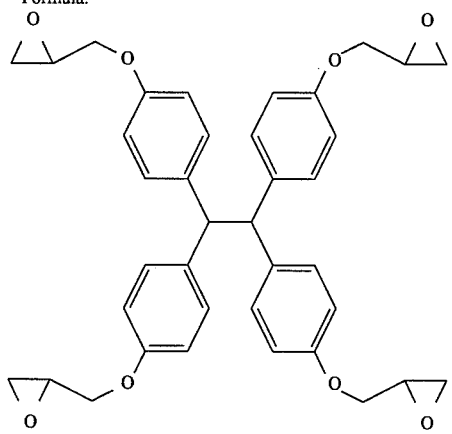

To prepare the advanced epoxy resins, a mixture of the bisphenol A diglycidyl ether and the diaminodiphenyl sulfone is first allowed to react at 150° C. for 2 hours. It is cooled to 130° C., the other components are added and the mixture is kept at 130° C. for a further 1 to 2 hours. The resin is then poured onto an aluminium sheet and cooled.

The powdered resin is mixed, melted and homogenized with the components which can be seen from the following table to give compositions Misch6, Misch7, Misch8 and Misch9.

These resin compositions are cast to sheets 1 mm or 2 mm thick and the sheets are cured fully at 180° C. for 1 hour. the resulting sheets have the properties shown in the subsequent table.

| | Misch6 | Misch7 | Misch8 | Misch9 |
|---|---|---|---|---|
| Component | | | | |
| Resin: No. | 6 | 7 | 8 | 9 |
| Amount | 100.00 | 100.00 | 100.00 | 100.00 |
| Polyglycidyl ether from Example 4 | 14.29 | — | — | 14.29 |
| Dicyandiamide | 4.57 | 4.00 | 4.00 | 4.57 |
| Other flame retardants[13] | 17,14 | 15,00 | 15,00 | 17,14 |
| Property | | | | |
| Tg 1[°C.] | 138 | 135 | 146 | 150 |
| Absorption of | 0.45 | 0.50 | 0.55 | 0.41 |

| | Misch6 | Misch7 | Misch8 | Misch9 |
|---|---|---|---|---|
| $H_2O^{14}$ [%] | | | | |
| Flame retardation[9] (1 mm sheet) | V-0 | V-0 | V-0 | V-0 |
| Bromine content [%] | 3.8 | 3.0 | 2.60 | 3.8 |
| Phosphorus content [%] | 1.78 | 1.78 | 1.78 | 1.78 |

[13] (2,6-Dimethylphenyl)2,2'-methylene-bis(6-tert-butyl-4-methylphenyl) phosphate (cf. Example 3 of EP-A-0 412 936)
[14] 2 mm thick sheet after 1 hour in hot water at 100° C.

EXAMPLE 6

Glycidylation of the Compound of Example 1

200 g (0.52 mol) of the compound of Example 1 are dissolved together with 92.53 g (1 mol) of epichlorohydrin in 385 g of methoxypropanol and are heated to 70° C. Then 22.88 g (0,572 mol) NaOH (as an 80% solution) are added dropwise within 80 minutes and the mixture is then stirred for further 2 hours at a temperature of 60° to 65° C. The obtained solution is neutralized with a 20% solution of sodium bisulfate. Then the solvent is entirely removed. The residue is again dissolved in isobutyl methyl ketone and filtered. The solvent is removed again under a high vacuum and the desired product is obtained in a yield of about 90%. It has an epoxy value of 1,81 equivalents/kg and a phosphorus content of 6.82%.

EXAMPLE 7

An 80% solution of an advanced resin is prepared from 100 g of the bisphenol A diglycidyl ether of Example 3, 26.5 g of the compound of Example 6, 6.00 g diaminodiphenylsulfone, 0,01 g 2-phenylimidazole and 33,13 g methyl ethyl ketone as it is described under Example 3.

125 g of this solution are mixed with 42.82 g of dicyandiamide (10% solution in methyl glycole), 20 g Cyagard®RF 1204, 40 g Apyral 4 and 0.04 g 2-methylimidazole. The gelling time of this impregnating solution is 295 s at 170° C. A laminate is prepared with this solution according to the description under Example 3 having the following properties:

| Property | | Property | |
|---|---|---|---|
| Tg 1[5] [°C.] | 152,3 | Flame retardation[9] | V-1 |
| Tg 2[5] [°C.] | 152,7 | | |
| Absorption of NMP[6] [%] | 0,12 | Burning time [s] | 68 |

[5,6,8,9] see under Example 3

What is claimed is:
1. A compound of the formula (1)

$$\begin{matrix} RO \\ (RO)_m \end{matrix} > T-[Z],$$  (1)

in which m is 0 or 1,

R is a hydrogen atom or a group of formula

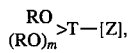

T is either an (m+2)-valent aromatic group having 6 to 14 ring carbon atoms or an (m+2)-valent group which is derived, by removal of (m+2) aromatic hydrogen atoms, from a compound of the formula (2)

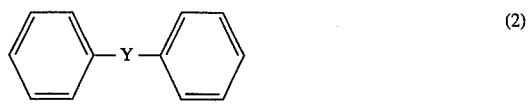

in which

Y is a chemical structural element selected from the group consisting of a single bond and the groups of the formula —O—, —S—, >SO$_2$, >C=O and

in which

R$^6$ and

R$^7$ independently of one another in each case are a hydrogen atom or a methyl group, and

[Z] is a group which comprises on average 1 to 10 structural units which are structural units of the formula (3)

in which

Q is a group of the formula (4)

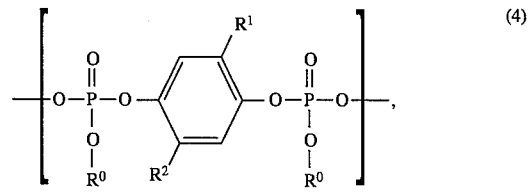

in which

R$^0$ is a radical of the formula (5)

R$^1$ and

R$^2$ and

R$^3$ independently of one another in each case are a C$_1$–C$_4$alkyl group,

R$^4$ is a hydrogen atom or a C$_1$–C$_4$alkyl group and

R$^5$ is a hydrogen, bromine or chlorine atom, a hydroxyl group or a group of formula

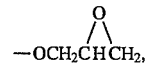

and in formula (3) furthermore

T has the same meaning as in formula 1,

EB symbolizes a free valency of the group T and r has one of the values 0, 1 or 1+m, and in which the structural units of the formula (3) are linked via their free valencies to the group [Z] such that the groups Q in each case alternate with groups T and the group [Z] overall is monovalent, with the proviso that [Z] is a group —[Q—T]$_k$—OR in which k is a value from 2 to 5 if m is 0.

2. A compound according to claim 1, in which m is 0.

3. A compound according to claim 2, in which

T is selected from the group consisting of 1,3-phenylene, 1,4-phenylene, 1,5-naphthylene and 2,2'-bis(4-phenylene)-propane.

4. A compound according to claim 1, in which m is 1.

5. A compound according to claim 1, in which m is 1 and

T is a group of the formula

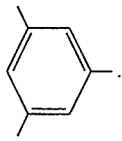

6. A compound according to claim 1, in which

[Z] is composed of 2 to 5 structural elements of the formula (3).

7. A compound according to claim 1, in which $R^5$ is a hydrogen atom, a hydroxyl group or a group of formula

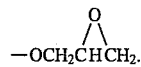

8. A compound according to claim 7, in which $R^5$ is a hydrogen atom.

9. A compound of the formula (1) according to claim 1, wherein R is a group of the formula

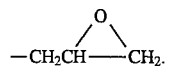

* * * * *